United States Patent [19]

Billotti

[11] Patent Number: 5,582,584
[45] Date of Patent: Dec. 10, 1996

[54] KNEE BRACE WITH SECURE ATTACHMENT AND METHOD

[76] Inventor: Joseph D. Billotti, 18 Powder Hill, Saddle River, N.J. 07458

[21] Appl. No.: 587,846

[22] Filed: Jan. 11, 1996

[51] Int. Cl.$^6$ ..................................................... A61F 5/01
[52] U.S. Cl. ........................ 602/26; 602/13; 128/DIG. 20
[58] Field of Search ................................. 602/23, 26, 5, 602/13, 19, 62, 63, 64; 128/DIG. 20

[56] References Cited

U.S. PATENT DOCUMENTS

| | | |
|---|---|---|
| 2,823,668 | 10/1953 | Van Court et al. . |
| 3,046,981 | 7/1962 | Biggs, Jr. et al. ........................ 602/26 |
| 3,853,123 | 12/1974 | Moore . |
| 3,955,565 | 5/1976 | Johnson, Jr. . |
| 4,084,584 | 4/1978 | Detty . |
| 4,219,892 | 9/1980 | Rigdon . |
| 4,263,905 | 4/1981 | Couch, Jr. . |
| 4,280,489 | 7/1981 | Johnson, Jr. . |
| 4,378,009 | 3/1983 | Rowley et al. . |
| 4,508,112 | 4/1985 | Seeler . |
| 4,597,384 | 7/1986 | Whitney . |
| 4,628,918 | 12/1986 | Johnson, Jr. . |
| 4,628,945 | 12/1986 | Johnson, Jr. . |
| 4,669,455 | 6/1987 | Bellati . |
| 4,682,588 | 7/1987 | Curlee ........................................ 602/13 |
| 4,703,750 | 11/1987 | Sebastian et al. . |
| 4,730,610 | 3/1988 | Graebe . |
| 4,805,606 | 2/1989 | McDavid, III ........................... 602/26 |
| 4,872,448 | 10/1989 | Johnson, Jr. . |
| 4,926,884 | 5/1990 | Lonardo . |
| 4,938,207 | 7/1990 | Vargo . |
| 4,953,569 | 9/1990 | Lonardo . |
| 4,961,418 | 10/1990 | McLaurin-Smith . |
| 5,016,621 | 5/1991 | Bender ..................................... 602/26 |
| 5,113,877 | 5/1992 | Johnson, Jr. et al. . |
| 5,125,400 | 6/1992 | Johnson, Jr. . |
| 5,230,695 | 7/1993 | Silver et al. . |
| 5,288,286 | 2/1994 | Davis et al. . |
| 5,378,224 | 1/1995 | Billotti . |
| 5,407,421 | 4/1995 | Goldsmith ........................... 602/23 X |
| 5,451,201 | 9/1995 | Prengler ............................... 602/13 X |

*Primary Examiner*—Richard J. Apley
*Assistant Examiner*—David R. Risley
*Attorney, Agent, or Firm*—Arthur Jacob

[57] ABSTRACT

A brace for supporting a weakened knee joint and a method for attaching the brace wherein lower and upper anchor bands are located upon and attached to the lower leg and the upper leg adjacent the knee joint, with essentially inextensible support straps following respective helical paths around the knee joint between the lower and upper anchor bands, and inflatable elements within the lower and upper anchor bands subsequently are inflated to anchor the attached lower and upper anchor bands in place for firm and accurate securement upon installation in the desired location and for maintaining the desired location during use.

15 Claims, 5 Drawing Sheets

KNEE BRACE WITH SECURE ATTACHMENT AND METHOD

The present invention relates generally to braces for supporting joints of the body and pertains, more specifically, to a knee brace having a secure attachment to the leg adjacent the knee being supported and a method for attaching the knee brace to the leg accurately, securely and with increased ease.

A large variety of braces has been made available for the support of body joints which have become weakened as a result of sports activity, accident, deterioration due to age, or disease. Braces for the knee are designed primarily to provide support while enabling the knee to function during normal activity. An important aspect in assuring proper operation of a knee brace is the ability of the brace to be secured in proper relation to the knee and to remain in place during use.

The present invention provides a brace which not only establishes the desired support for a weakened knee, but enables secure placement with increased accuracy, reliability, ease and comfort. As such, the present invention attains several objects and advantages, some of which are summarized as follows: Provides effective support to a weakened knee with minimal interference with the functioning of the knee during normal activity; enables increased ease of placement and securement in appropriate position in relation to the knee, with increased accuracy of placement; provides a secure attachment to the leg for maintaining the brace accurately in place during use; enables ease of attachment and detachment through simplified multiple steps for encouraging proper use; attains a higher degree of comfort both during installation and during use, with ease of adjustment to maintain proper placement as well as comfort; provides a simplified construction which is economical to manufacture and attains reliable performance over an extended service life.

The above objects and advantages, as well as further objects and advantages, are attained by the present invention which may be described briefly as a brace to be attached to an upper leg and a lower leg of a body for supporting a weakened knee joint located between the upper leg and the lower leg, the brace comprising: a lower anchor band extending in a lateral direction between opposite ends for being located upon the lower leg, adjacent the knee, the lower anchor band including a lower front segment having a laterally extending upper edge and an opposite laterally extending lower edge spaced altitudinally from the upper edge, and lower band securing means for securing the lower anchor band located upon the lower leg; a first strap integral with the lower front segment adjacent the upper edge and projecting from the lower front segment at an acute angle to the lateral direction to extend generally toward one of the opposite ends of the lower anchor band for following a first helical path around the knee; a first upper anchor band integral with the first strap and spaced away from the upper edge of the lower front segment of the lower anchor band, the first upper anchor band extending laterally for being located along the upper leg, adjacent the knee, and including first upper anchor band securing means for securing the first upper anchor band in the location along the upper leg, with the first strap following the first helical path; a second strap integral with the lower front segment adjacent the upper edge and projecting from the lower front segment at an acute angle to the lateral direction to extend generally toward the other of the opposite ends of the lower anchor band for following a second helical path around the knee, the second helical path being opposite to the first helical path; a second upper anchor band integral with the second strap and spaced away from the upper edge of the lower front segment of the lower anchor band, the second upper anchor band extending laterally for being located along the upper leg, adjacent the knee, and including second upper band securing means for securing the second upper anchor band at the location along the upper leg, with the second strap following the second helical path; lower inflatable means in the lower anchor band for selective inflation when the lower anchor band is located along the lower leg to grip the lower leg and anchor the lower anchor band to the lower leg; and upper inflatable means in at least one of the first upper anchor band and the second upper anchor band for selective inflation when the first and second upper anchor bands are located along the upper leg to grip the upper leg and anchor the first and second upper anchor bands to the upper leg; the first and second straps being essentially inextensible such that upon anchoring the lower anchor band to the lower leg, the first upper anchor band to the upper leg and the second upper anchor band to the upper leg, with the first and second straps following the respective first and second helical paths, the first and second straps support the weakened knee joint. Further, the present invention includes a method for attaching a brace to an upper leg and a lower leg of a body for supporting a weakened knee joint located between the upper leg and the lower leg, the method comprising: locating a lower anchor band upon the lower leg, adjacent the knee, the lower anchor band including a lower front segment having a laterally extending upper edge; securing the lower anchor band located around the lower leg; wrapping a first strap around the knee, the first strap being integral with the lower front segment adjacent the upper edge and projecting from the lower front segment at an acute angle to the lateral direction to extend generally toward one of the opposite ends of the lower anchor band so as to follow a first helical path around the knee upon wrapping the first strap around the knee; locating a first upper anchor band upon the upper leg, the first upper anchor band being integral with the first strap and spaced away from the upper edge of the lower front segment of the lower anchor band, the first upper anchor band extending laterally for extending in the direction around the upper leg, adjacent the knee; securing the first upper anchor band upon the upper leg, with the first strap following the first helical path; wrapping a second strap around the knee, the second strap being integral with the lower front segment adjacent the upper edge and projecting from the lower front segment at an acute angle to the lateral direction to extend generally toward the other of the opposite ends of the lower anchor band so as to follow a second helical path around the knee, the second helical path being opposite to the first helical path; locating a second upper anchor band upon the upper leg, the second upper anchor band being integral with the second strap and spaced away from the upper edge of the lower front segment of the lower anchor band, the second upper anchor band extending laterally for extending in the direction around the upper leg, adjacent the knee; securing the second upper anchor band upon the upper leg, with the second strap following the second helical path; inflating lower inflatable means in the lower anchor band when the lower anchor band is located around the lower leg so as to grip the lower leg and anchor the lower anchor band to the lower leg; and inflating upper inflatable means in at least one of the first upper anchor band and the second upper anchor band when the first and second upper anchor bands are located upon the upper leg so as to grip the upper leg and anchor the first and second upper anchor bands upon the upper leg; the first and second straps being essentially inextensible such that upon anchoring the lower anchor band upon the lower leg, the first upper anchor band upon the upper leg and the second upper anchor band upon the upper leg, with the first and second straps following the respective first and second helical paths, the first and second straps support the weakened knee joint.

The invention will be understood more fully, while still further objects and advantages will become apparent, in the following detailed description of a preferred embodiment of the invention illustrated in the accompanying drawing, in which.

Figure 1:
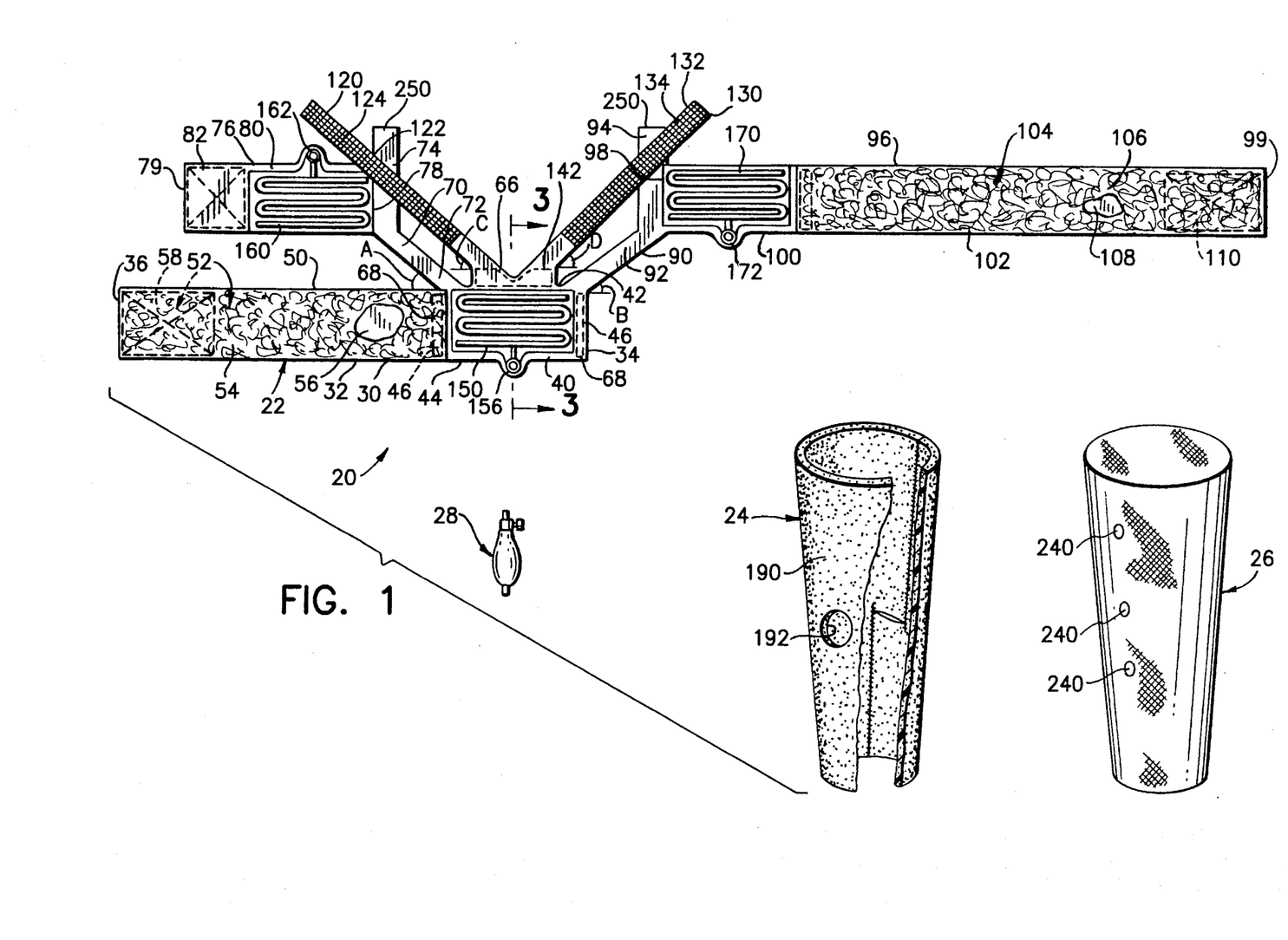
FIG. 1 is a pictorial illustration of component parts of a knee brace constructed in accordance with the present invention, including a front elevational view of the support component of the knee brace.
Figures 2, 3:
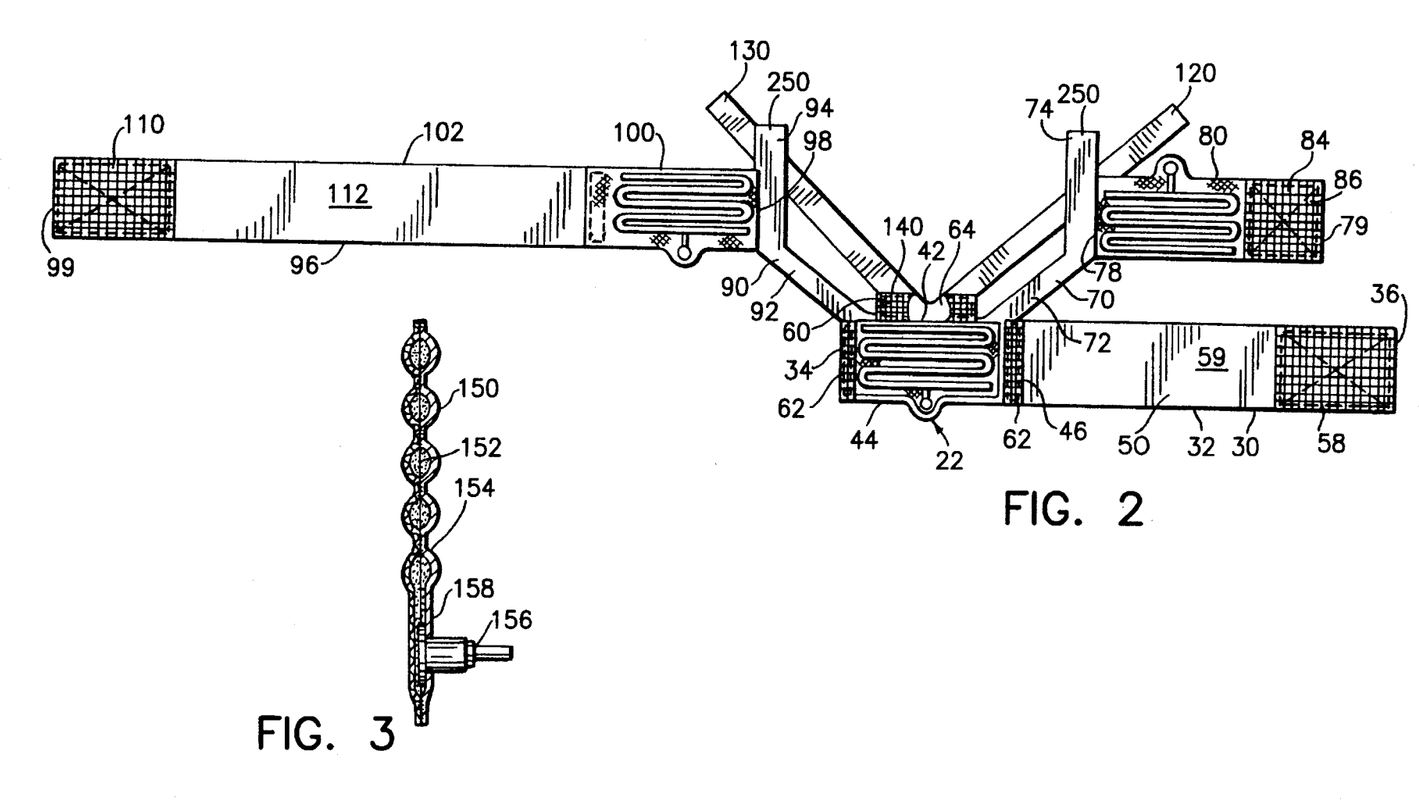
FIG. 2 is a rear elevational view of the support component.
FIG. 3 is an enlarged cross-sectional view taken along line 3—3 of FIG. 1.

Referring now to the drawing, and especially to FIGS. 1 and 2 thereof, a knee brace constructed in accordance with the present invention is illustrated at 20 and is seen to include a support component 22, an inner sleeve 24, and an outer sleeve 26. An air pump 28 is an additional component part utilized in connection with the knee brace 20, as will be explained in detail below.

Support component 22 includes a member 30 in the form of a relatively thin sheet of flexible and essentially inextensible synthetic polymeric material, such as a commercially available nylon fabric coated on one side with a polyurethane film, the term "essentially inextensible" meaning that the material resists stretching in response to tensile loads, while remaining flexible. Member 30 includes a lower anchor band 32 extending in a lateral direction between opposite ends 34 and 36. A lower front segment 40 of the lower anchor band 32 extends laterally from the end 34 toward the end 36 and has a laterally extending upper edge 42, an opposite laterally extending lower edge 44 spaced altitudinally from the upper edge 42, and laterally opposite side edges 46. Lower anchor band 32 includes securing means in the form of a securing segment 50 extending laterally from the lower front segment 40 to the end 36 and carrying a hook-and-loop fastener 52 having an elongate loop element 54, extending along a front face 56 of the securing segment 50 from the lower front segment 40 to the end 36, and a hook element 58 extending along a rear face 59 of the securing segment 50 from the end 36 toward the lower front segment 40. A suitable hook-and-loop fastener is available under the trademark VELCRO.

Locator means are placed at upper edge 42 and at each side edge 46 of the lower front segment 40 and are shown in the form of hook elements 60 and 62 of a hook-and-loop fastener, the hook elements 60 and 62 being affixed to the lower front segment 40, at a rear face 64 thereof, along the upper edge 42 and along the opposite side edges 46, as by sewing at 66 and at 68, respectively, or otherwise permanently attaching the hook elements 60 and 62 to the lower front segment 40.

A first strap 70 is integral with the lower front segment 40 of the lower anchor band 32 adjacent the upper edge 42 and projects from the lower front segment 40 at an acute angle A to the lateral direction to extend generally toward the end 36 of the lower anchor band 32. First strap 70 includes an intermediate segment 72 extending along the direction of angle A, and a terminal segment 74 extending in an altitudinal direction, generally parallel to side edges 46 and normal to the upper edge 42. A first upper anchor band 76 is integral with the first strap 70 and is spaced away from the upper edge 42 of the lower front segment 40 of the lower anchor band 32 by an altitudinal distance determined by the length of the intermediate segment 72 and the angle A, the first upper anchor band 76 extending laterally, generally parallel to the lower anchor band 32, between opposite ends 78 and 79. First upper anchor band 76 includes a first upper front segment 80 extending laterally from the end 78, at the terminal segment 74, toward the end 79 and securing means in the form of a securing segment 82 extending laterally from the first upper front segment 80 to the end 79 and carrying a hook element 84 of a hook-and-loop fastener, the hook element 84 extending along a rear face 86 of the securing segment 82 from the end 79 toward the first upper front segment 80.

A second strap 90 is integral with the lower front segment 40 of the lower anchor band 32 adjacent the upper edge 42 and projects from the lower front segment 40 at an acute angle B to the lateral direction to extend generally toward the end 34 of the lower anchor band 32. Second strap 90 includes an intermediate segment 92 extending along the direction of angle B, and a terminal segment 94 extending in an altitudinal direction. A second upper anchor band 96 is integral with the second strap 90 and is spaced away from the upper edge 42 of the lower front segment 40 of the lower anchor band 32 by an altitudinal distance determined by the length of the intermediate segment 92 and the angle B, the second upper anchor band 96 extending laterally, generally parallel to the lower anchor band 32, between opposite ends 98 and 99. Second upper anchor band 96 includes a second upper front segment 100 extending laterally from the end 98, at the terminal segment 94, toward the 5 end 99 and securing means in the form of a securing segment 102 extending laterally from the second upper front segment 100 to the end 99 and carrying a hook-and-loop fastener 104 having an elongate loop element 106, extending along a front face 108 of the securing segment 102 from the front segment 100 to the end 99, and a hook element 110 extending along a rear face 112 of the securing segment 102 from the end 99 toward the second upper front segment 100. A suitable hook-and-loop fastener is available under the trademark VELCRO. Thus, the first and second straps 70 and 90 are in a V-shaped array, radiating from the upper edge 42 of the lower front segment 40 of the lower anchor band 32.

A first auxiliary strap 120 is integral with the lower front segment 40 of the lower anchor band 32, adjacent the upper edge 42 thereof, and projects from the lower front segment 40 at an acute angle C to the lateral direction to extend generally toward end 36 of the lower anchor band 32. First auxiliary securing means are shown in the form of a securing segment 122 extending along the first auxiliary strap 120 and carrying a hook element 124 of a hook-and-loop fastener. A second auxiliary strap 130 is integral with the lower front segment 40 of the lower anchor band 32, adjacent the upper edge 42 thereof, and projects from the lower front segment 40 at an acute angle D to the lateral direction to extend generally toward end 34 of the lower anchor band 32. Second auxiliary securing means are shown in the form of a securing segment 132 extending along the second auxiliary strap 130 and carrying a hook element 134 of a hook-and-loop fastener. Thus, the first and second auxiliary straps 120 and 130 are in a V-shaped array, located between the V-shaped array followed by the first and second straps 70 and 90.

In the preferred embodiment illustrated in the drawing, the first and second straps 70 and 90 are constructed unitary with the lower front segment 40, while the auxiliary straps 120 and 130 are affixed to a tab 140 constructed unitary with the lower front segment 40, as by sewing at 142 or otherwise joining the auxiliary straps 120 and 130 with the tab 140 to render the auxiliary straps 120 and 130 integral with the lower front segment 40.

As best seen in FIG. 3, as well as in FIGS. 1 and 2, the lower anchor band 32 includes inflatable means in the form of bladder 150 in the lower front segment 40 of the lower anchor band 32, the bladder 150 having a sinuous internal passage 152 established by affixing a bladder sheet 154 to the sheet material of member 30 at the lower front segment 40, along a sinuous pattern, as by laminating or welding the bladder sheet 154 to the member 30 along the sinuous pattern, to construct the passage 152. A valve 156 communicates with the passage 152 of the bladder 150, through a feed passage 158, and normally closes communication to the bladder 150. Selective opening of the valve 156 enables access to the passage 152 of the bladder 150 for selectively inflating and deflating the bladder 150, to alternately expand and contract the lower front segment 40 in directions normal to the lateral and altitudinal directions; that is, normal to the plane of the paper in FIGS. 1 and 2.

Similarly, first upper anchor band 76 includes inflatable means in the form of a bladder 160 located in first upper front segment 80 and constructed in the manner described above in connection with bladder 150 for selective inflation and deflation through a valve 162. Likewise, second upper anchor band 96 includes inflatable means in the form of a bladder 170 located in second upper front segment 100 and constructed in the manner described above in connection with bladder 150 for selective inflation and deflation through a valve 172.

Turning now to FIGS. 4 through 8, knee brace 20 is applied to a knee 180 as follows: First, inner sleeve 24 is slipped over the knee 180 to extend along the adjacent upper leg 182 and lower leg 184. To this end, inner sleeve 24 is constructed of a pliable and somewhat stretchable material, the material providing an outer surface 190 having surface characteristics which allow the attachment of a hook element of a hook-and-loop fastener to the outer surface 190, for purposes to be described in detail hereinafter. The preferred material for inner sleeve 24 is a commercially available material having a core of closed-cell foam rubber laminated with an inner layer of stretchable nylon material and an outer layer of nylon material rendered compatible with a VELCRO fastener element. One such material is available from Rubatex Company located in Bedford, Va. When in place, the inner sleeve 24 fits snugly over the knee 180, and an opening 192 in the inner sleeve 24 provides clearance for the patella of the knee 180.

Figure 4:
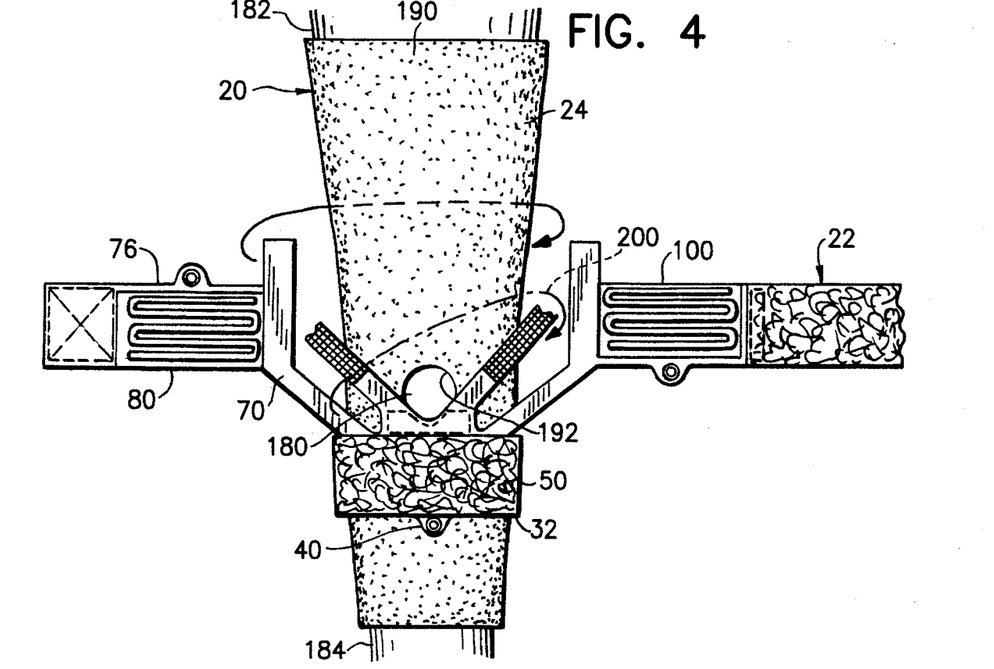
FIGS. 4 through 10 are elevational views illustrating various stages of attachment of the knee brace.

Once the inner sleeve 24 is fitted over the knee 180, as described above, the support component 22 is placed over the inner sleeve 24 as follows: The lower front segment 40 of the lower anchor band 32 is located along the anterior of the lower leg 184 and is held in place by the hook elements 60 at the upper edge 42 and the hook elements 62 at the side edges 46 of the lower front segment 40, which hook elements 60 and 62 grasp the material of the inner sleeve 24 along outer surface 190 to hold the lower front segment 40 in place for completion of the next step. Then, the securing segment 50 is wrapped around the lower leg 184 and over the lower front segment 40, and the hook element 58 is engaged with the loop element 54 of the hook-and-loop fastener 52 to secure the lower anchor band 32 in place.

Figure 5:
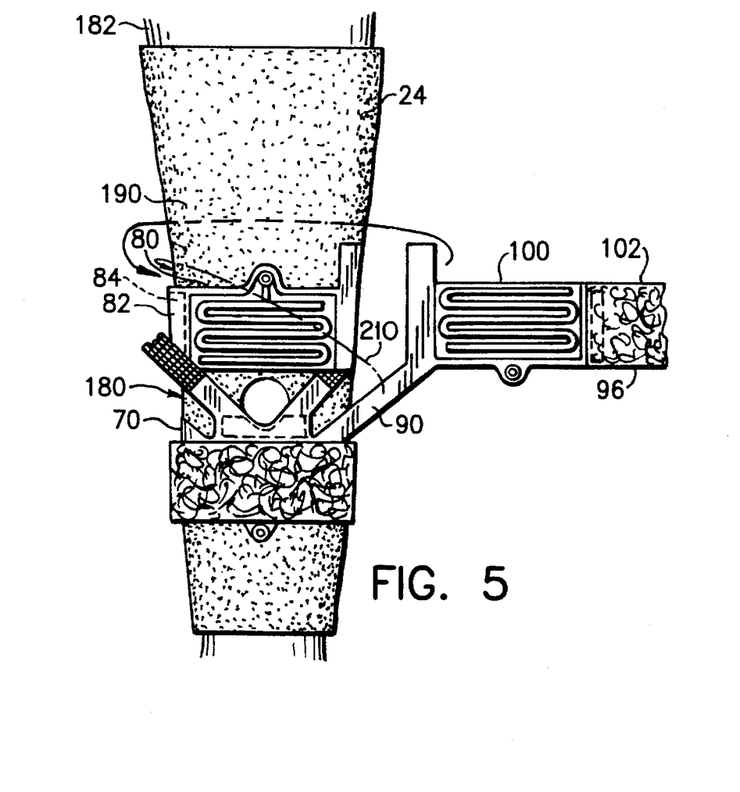
Figures 6, 7:
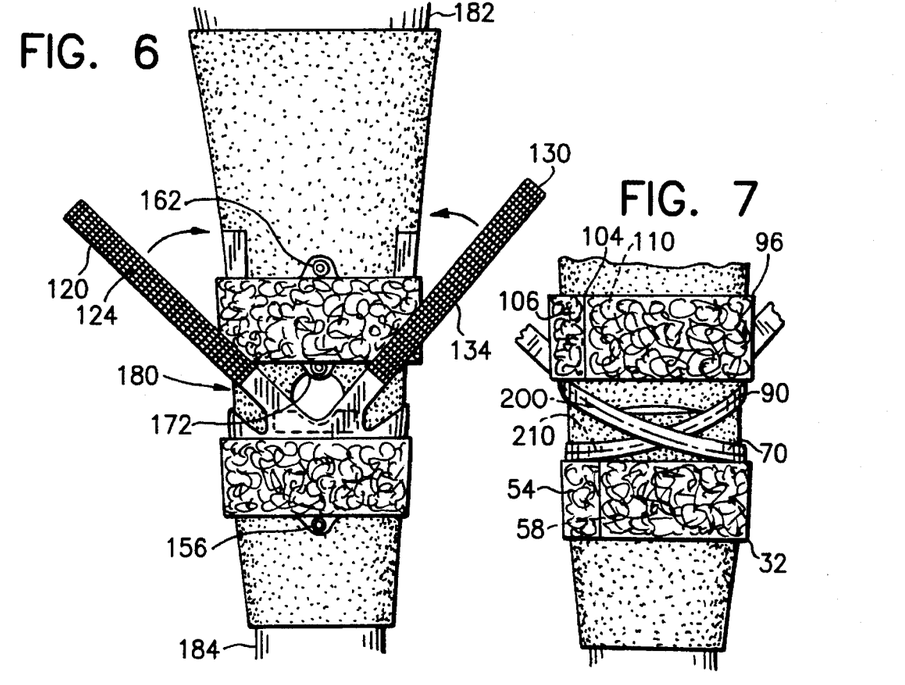

Next, the first strap 70 is wound along a first helical path 200, as seen in FIG. 4, with the helical path 200 extending behind the knee 180, as seen in FIG. 7, the first upper front segment 80 of the first upper anchor band 76 is placed along the anterior of the upper leg 182 and the securing segment 82 of the first upper anchor band 76 is located upon the upper leg 182, where the first upper anchor band 76 is secured in place, overlying the inner sleeve 24, by attaching the hook element 84 of the securing segment 82 to the outer surface 190 of the inner sleeve 24, as seen in FIG. 5.

Then, the second strap 90 is wound along a second helical path 210, as seen in FIG. 5, with the second helical path 210 extending behind the knee 180, as seen in FIG. 7, the second upper front segment 100 of the second upper anchor band 96 is placed along the anterior of the upper leg 182, overlying the first upper front segment 80, and the securing segment 102 of the second upper anchor band 96 is wrapped around the upper leg 182, over the first upper anchor band 76, to engage the hook element 110 of the second upper anchor band 96 with the loop element 106 of the hook-and-loop fastener 104, thereby securing the second upper anchor band 96 in place, overlying the first upper anchor band 76 and the inner sleeve 24, as seen in FIGS. 6 and 7. The length of the second upper anchor band 96 between the ends 98 and 99 is somewhat greater than the corresponding length of the lower anchor band 32 between the ends 34 and 36 in order to accommodate the greater girth of the upper leg 182, as compared to the lesser girth of the lower leg 184. Note that the placement of the front segments 40, 80 and 100 locates the valves 156, 162 and 172 essentially aligned longitudinally along the anterior of the upper and lower legs 182 and 184, as illustrated in FIG. 8 and exposes each valve for purposes to be described below.

Figure 8:
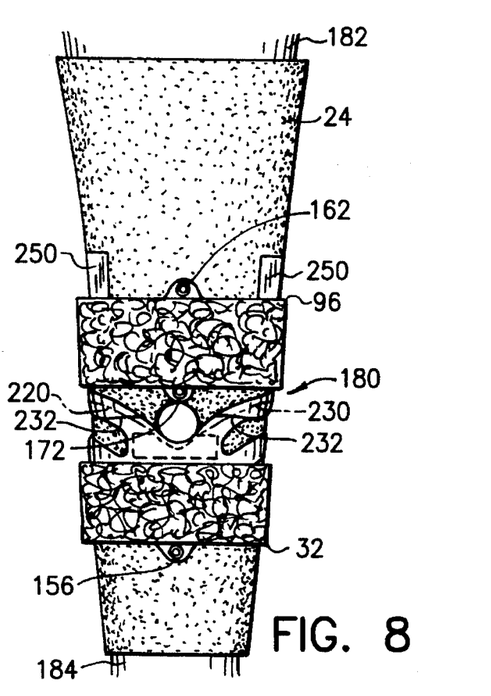
Figure 9:
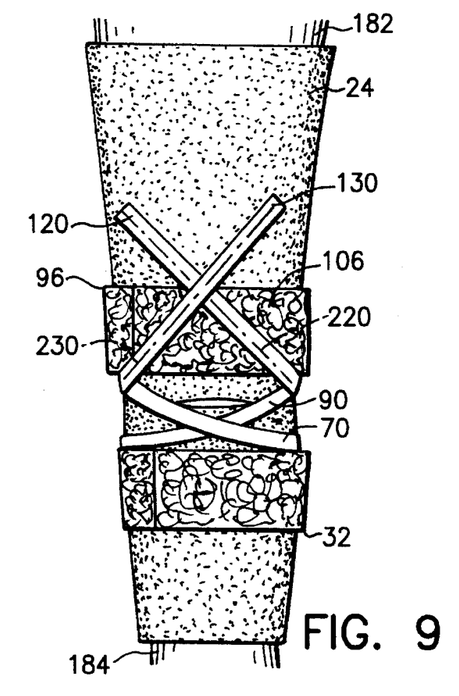

Next, the auxiliary straps 120 and 130 are wound around the knee 180, along respective helical paths 220 and 230, as illustrated in FIGS. 6 through 8, and are secured in place by engaging the hook elements 124 and 134 of the auxiliary straps 120 and 130, respectively, with the loop element 106 of the second upper anchor band 96, as best seen in FIG. 9. The auxiliary straps 120 and 130 each are provided with a twist, at 232, to direct the pull of auxiliary straps 120 and 130 more toward the posterior direction so as to provide support for the lower leg 184, and consequently the upper tibia, which braces against anterior subluxation of the tibia.

Figure 10:
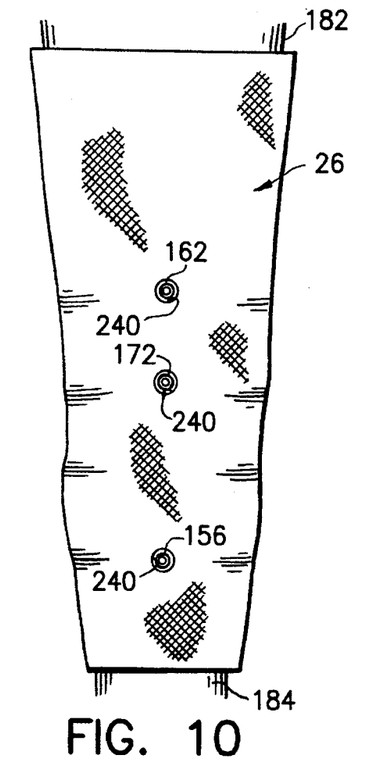
Figure 11:
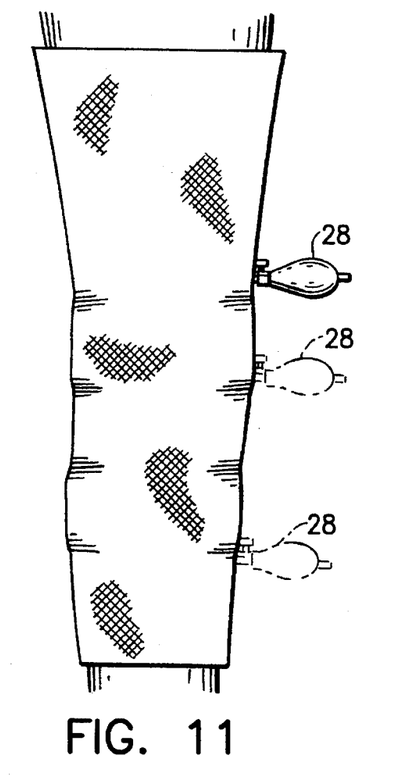
FIG. 11 is a side elevational view similar to FIG. 10, but illustrating another stage of attachment.

Once all of the straps 70, 90, 120 and 130 are in place, as described above, the outer sleeve 26 is located over the support component 22 so as to be placed as shown in FIGS. 10 and 11. Outer sleeve 26 is constructed in the form of a relatively thin sheath of a resiliently expansible material, such as LYCRA, and is slipped, stocking-like, over the support component 22 which has been installed as described above. Apertures 240 in the outer sleeve 26 are registered with respective valves 156, 162 and 172, so that the valves 156, 162 and 172 each extend through the outer sleeve 26 for selective coupling with the air pump 28. The air pump 28 then is employed to inflate the bladders 150, 160 and 170, thereby increasing the grip of the previously located anchor bands 32, 76 and 96 and firmly anchoring the respective anchor bands 32, 76 and 96 in the appropriate location. The firm anchoring of the anchor bands 32, 76 and 96 fixes the placement of the first and second straps 70 and 90 and the first and second auxiliary straps 120 and 130, and secures the support component 22 in place for appropriate bracing of the knee 180. The construction of knee brace 20 enables the separate steps of locating the lower and upper anchor bands 32, 76 and 96, and the several straps 70, 90, 120 and 130 in appropriate placement relative to the knee 180 with ease, and then firmly anchoring the anchor bands 32, 76 and 96 to secure that placement by subsequent inflation of the several inflatable means, while maintaining the combination of flexibility and relative inextensibility in the straps 70, 90, 120 and 130. In this manner, accuracy is attained with increased ease in the initial location of the knee brace 20 and in the maintenance of that location during use, with increased comfort.

Figure 12:
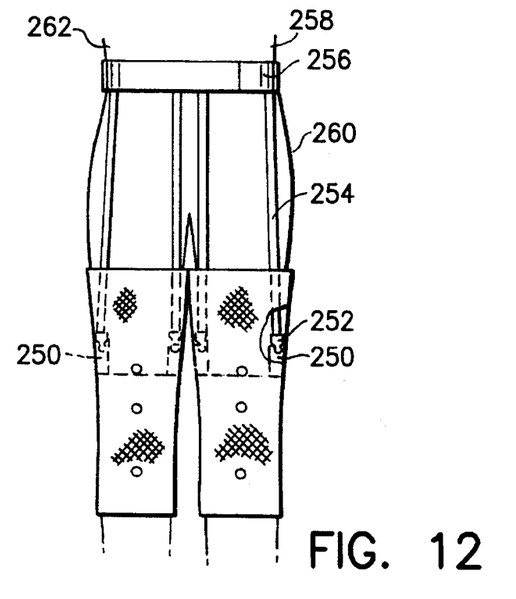
FIG. 12 is a front elevational view showing knee braces attached to a wearer and incorporating supplemental supports.

Turning now to FIG. 12, as an additional feature in assisting in maintaining the knee brace 20 in place at the knee 180, a support tab 250 projects upwardly from each of the terminal segments 74 and 94 of each of the first and second straps 70 and 90, respectively, for engagement by a clip 252 suspended by a tether 254 from a belt 256 at the waist 258 of the body 260 of a wearer 262, to assist in maintaining the support component 22 in place.

It will be seen that the present invention attains the several objects and advantages summarized above, namely: Provides effective support to a weakened knee with minimal interference with the functioning of the knee during normal activity; enables increased ease of placement and securement in appropriate position in relation to the knee, with increased accuracy of placement; provides a secure attachment to the leg for maintaining the brace accurately in place during use; enables ease of attachment and detachment through simplified multiple steps for encouraging proper use; attains a higher degree of comfort both during installation and during use, with ease of adjustment to maintain proper placement as well as comfort; provides a simplified construction which is economical to manufacture and attains reliable performance over an extended service life.

It is to be understood that the above detailed description of preferred embodiments of the invention is provided by way of example only. Various details of design and construction may be modified without departing from the true spirit and scope of the invention, as set forth in the appended claims.

The embodiments of the invention in which an exclusive property or privilege is claimed are defined as follows:

1. A brace to be attached to an upper leg and a lower leg of a body for supporting a weakened knee joint located between the upper leg and the lower leg, the brace comprising:

a lower anchor band extending in a lateral direction between opposite ends for being located upon the lower leg, adjacent the knee, the lower anchor band including a lower front segment having a laterally extending upper edge and an opposite laterally extending lower edge spaced altitudinally from the upper edge, and lower band securing means for securing the lower anchor band located upon the lower leg;

a first strap integral with the lower front segment adjacent the upper edge and projecting from the lower front segment at an acute angle to the lateral direction to extend generally toward one of the opposite ends of the lower anchor band for following a first helical path around the knee;

a first upper anchor band integral with the first strap and spaced away from the upper edge of the lower front segment of the lower anchor band, the first upper anchor band extending laterally for being located along the upper leg, adjacent the knee, and including first upper anchor band securing means for securing the first upper anchor band in the location along the upper leg, with the first strap following the first helical path;

a second strap integral with the lower front segment adjacent the upper edge and projecting from the lower front segment at an acute angle to the lateral direction to extend generally toward the other of the opposite ends of the lower anchor band for following a second helical path around the knee, the second helical path being opposite to the first helical path;

a second upper anchor band integral with the second strap and spaced away from the upper edge of the lower front segment of the lower anchor band, the second upper anchor band extending laterally for being located along the upper leg, adjacent the knee, and including second upper band securing means for securing the second upper anchor band at the location along the upper leg, with the second strap following the second helical path;

lower inflatable means in the lower anchor band for selective inflation when the lower anchor band is located along the lower leg to grip the lower leg and anchor the lower anchor band to the lower leg; and upper inflatable means in at least one of the first upper anchor band and the second upper anchor band for selective inflation when the first and second upper anchor bands are located along the upper leg to grip the upper leg and anchor the first and second upper anchor bands to the upper leg;

the first and second straps being essentially inextensible such that upon anchoring the lower anchor band to the lower leg, the first upper anchor band to the upper leg and the second upper anchor band to the upper leg, with the first and second straps following the respective first and second helical paths, the first and second straps support the weakened knee joint.

2. The invention of claim 1 including:

first upper inflatable means in the first upper anchor band for selective inflation when the first upper anchor band is located along the upper leg to grip the upper leg and anchor the first upper anchor band to the upper leg; and second upper inflatable means in the second upper anchor band for selective inflation when the second upper anchor band is located along the upper leg to grip the upper leg and anchor the upper anchor band to the upper leg.

3. The invention of claim 1 including:

a first auxiliary strap integral with the lower front segment adjacent the upper edge of the lower front segment and projecting from the front segment at an acute angle to the lateral direction to extend generally toward one of the opposite ends of the lower anchor band for following a first auxiliary helical path around the knee, the first auxiliary strap including first auxiliary securing means for securing the first auxiliary strap wrapped around the knee, with the first auxiliary strap following the first auxiliary helical path; and a second auxiliary strap integral with the lower front segment adjacent the upper edge of the lower front segment and projecting from the lower front segment at an acute angle to the lateral direction to extend generally toward the other of the opposite ends of the lower anchor band for following a second auxiliary helical path around the knee, the second auxiliary helical path being opposite to the first auxiliary helical path, the second auxiliary strap including second auxiliary securing means for securing the second auxiliary strap wrapped around the knee, with the second auxiliary strap following the second auxiliary helical path;

the first and second auxiliary straps being located between the first and second straps.

4. The invention of claim 1 wherein the first upper anchor band has a first lateral extent, and the second upper anchor band has a second lateral extent greater than the first lateral extent for wrapping the second upper anchor band around the upper leg, over the first upper anchor band.

5. The invention of claim 1 including an inner sleeve of resilient material for fitting over the knee, over the lower leg adjacent the knee and the over the upper leg adjacent the knee, to underlie the lower anchor band, the first upper anchor band and the second upper anchor band, with the inner sleeve juxtaposed between the knee, the lower leg and the upper leg, and the lower anchor band, the first upper anchor band, the second upper anchor band, and the first and second straps.

6. The invention of claim 5 including an outer sleeve of resilient material for placement over the inner sleeve and the juxtaposed lower anchor band, first upper anchor band, second upper anchor band and the first and second straps.

7. The invention of claim 1 including an upper front segment in at least one of the first upper anchor band and the second upper anchor band, the upper inflatable means being located in the upper front segment.

8. The invention of claim 1 including:

a first upper front segment in the first upper anchor band;

a second upper front segment in the second upper anchor band;

a first upper inflatable means located in the first upper front segment; and a second upper inflatable means located in the second upper front segment.

9. The invention of claim 1 wherein the first and second straps project from the lower front segment in a V-shaped array.

10. The invention of claim 9 including:

a first auxiliary strap integral with the lower front segment adjacent the upper edge of the lower front segment and projecting from the front segment at an acute angle to the lateral direction to extend generally toward one of the opposite ends of the lower anchor band for following a first auxiliary helical path around the knee, the first auxiliary strap including first auxiliary securing means for securing the first auxiliary strap wrapped around the knee, with the first auxiliary strap following the first auxiliary helical path; and a second auxiliary strap integral with the lower front segment adjacent the upper edge of the lower front segment and projecting from the lower front segment at an acute angle to the lateral direction to extend generally toward the other of the opposite ends of the lower anchor band for following a second auxiliary helical path around the knee, the second auxiliary helical path being opposite to the first auxiliary helical path, the second auxiliary strap including second auxiliary securing means for securing the second auxiliary strap wrapped around the knee, with the second auxiliary strap following the second auxiliary helical path;

the first and second auxiliary straps projecting from the lower front segment in a V-shaped array located between the first and second straps.

11. A method for attaching a brace to an upper leg and a lower leg of a body for supporting a weakened knee joint located between the upper leg and the lower leg, the method comprising:

locating a lower anchor band upon the lower leg, adjacent the knee, the lower anchor band including a lower front segment having a laterally extending upper edge;

securing the lower anchor band located around the lower leg;

wrapping a first strap around the knee, the first strap being integral with the lower front segment adjacent the upper edge and projecting from the lower front segment at an acute angle to the lateral direction to extend generally toward one of the opposite ends of the lower anchor band so as to follow a first helical path around the knee upon wrapping the first strap around the knee;

locating a first upper anchor band upon the upper leg, the first upper anchor band being integral with the first strap and spaced away from the upper edge of the lower front segment of the lower anchor band, the first upper anchor band extending laterally for extending in the direction around the upper leg, adjacent the knee;

securing the first upper anchor band upon the upper leg, with the first strap following the first helical path;

wrapping a second strap around the knee, the second strap being integral with the lower front segment adjacent the upper edge and projecting from the lower front segment at an acute angle to the lateral direction to extend generally toward the other of the opposite ends of the lower anchor band so as to follow a second helical path around the knee, the second helical path being opposite to the first helical path;

locating a second upper anchor band upon the upper leg, the second upper anchor band being integral with the second strap and spaced away from the upper edge of the lower front segment of the lower anchor band, the second upper anchor band extending laterally for extending in the direction around the upper leg, adjacent the knee;

securing the second upper anchor band upon the upper leg, with the second strap following the second helical path;

inflating lower inflatable means in the lower anchor band when the lower anchor band is located around the lower leg so as to grip the lower leg and anchor the lower anchor band to the lower leg; and inflating upper inflatable means in at least one of the first upper anchor band and the second upper anchor band when the first and second upper anchor bands are located upon the upper leg so as to grip the upper leg and anchor the first and second upper anchor bands upon the upper leg;

the first and second straps being essentially inextensible such that upon anchoring the lower anchor band upon the lower leg, the first upper anchor band upon the upper leg and the second upper anchor band upon the upper leg, with the first and second straps following the respective first and second helical paths, the first and second straps support the weakened knee joint.

12. The invention of claim 11 wherein the second upper anchor band is wrapped over the first upper anchor band.

13. The invention of claim 11 including:

wrapping a first auxiliary strap around the knee, the first auxiliary strap being integral with the lower front segment adjacent the upper edge of the lower front segment and projecting from the front segment at an acute angle to the lateral direction to extend generally toward one of the opposite ends of the lower anchor band so as to follow a first auxiliary helical path around the knee;

securing the first auxiliary strap wrapped around the knee, with the first auxiliary strap following the first auxiliary helical path;

wrapping a second auxiliary strap around the knee, the second auxiliary strap being integral with the lower front segment adjacent the upper edge of the lower front segment and projecting from the lower front segment at an acute angle to the lateral direction to extend generally toward the other of the opposite ends of the lower anchor band so as to follow a second auxiliary helical path around the knee, the second auxiliary helical path being opposite to the first auxiliary helical path; and securing the second auxiliary strap wrapped around the knee, with the second auxiliary strap following the second auxiliary helical path;

the first and second auxiliary straps being located between the first and second straps.

14. The invention of claim 11 including fitting an inner sleeve of resilient material over the knee, over the lower leg adjacent the knee and the over the upper leg adjacent the knee, prior to wrapping the lower anchor band around the lower leg, to underlie the lower anchor band, the first upper anchor band and the second upper anchor band, with the inner sleeve juxtaposed between the knee, the lower leg and the upper leg, and the lower anchor band, the first upper anchor band, the second upper anchor band, and the first and second straps.

15. The invention of claim 11 including placing an outer sleeve of resilient material over the inner sleeve and the juxtaposed lower anchor band, first upper anchor band, second upper anchor band and the first and second straps, prior to inflation of the lower and upper inflatable means.

\* \* \* \* \*